April 20, 1965 H. W. MOTZKAU Plant Pat. 2,495
AZALEA PLANT
Filed Sept. 5, 1963
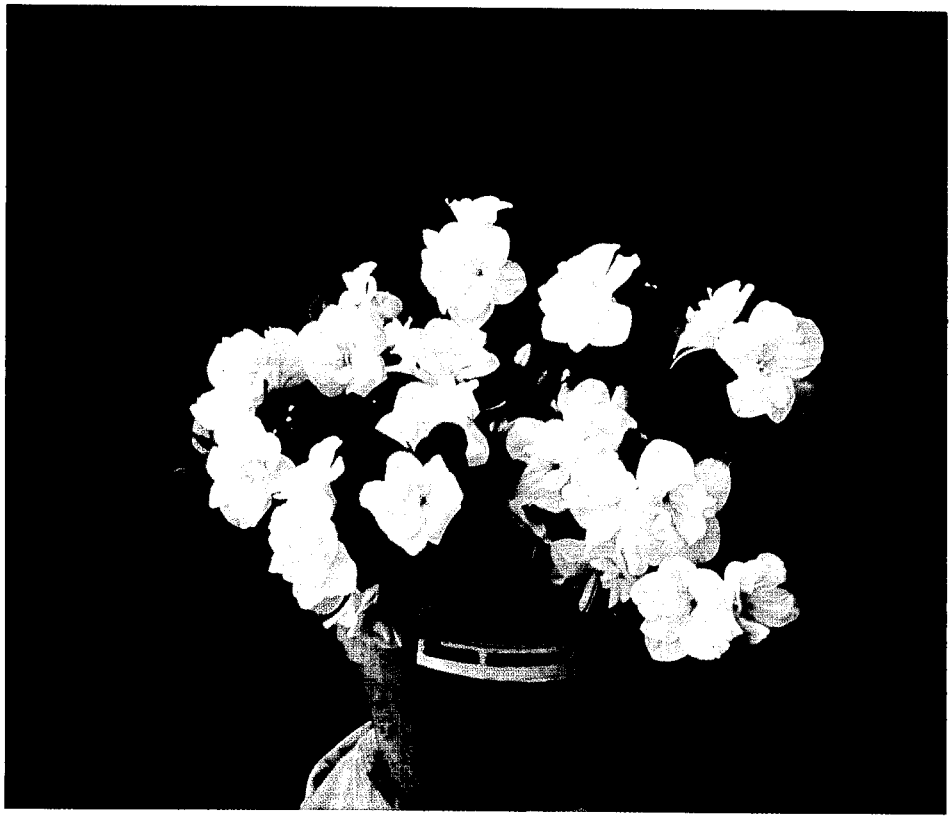
INVENTOR
H. W. MOTZKAU
By Robb & Robb
attorneys United States Patent Office Plant Pat. 2,495
Patented Apr. 20, 1965

2,495
AZALEA PLANT

Henry W. Motzkau, Whitewater, Wis., assignor to Yeder Brothers, Inc., Barberton, Ohio, a corporation of Ohio Filed Sept. 5, 1963, Ser. No. 306,969
1 Claim. (Cl. Plt.—55)

My present invention comprises a new and distinct variety of azalea plant developed in a program of hybridization by crossing a variety of my own origination which I designate as #449 with another variety of my own origination, which I designate as #302, neither variety being patented, in an endeavor to obtain some improved characteristics over either of the said varieties.

The object of this invention is to produce a new variety of azalea plant which will bloom early and being white, is in decided contrast to the traits found in other white azaleas, which ordinarily do not bloom in time for the Christmas season.

The particular azalea plant hereof is one of the variety which has been bred to approach the showiness of *Azalea indica* but to overcome the production difficulty caused by the relatively slow growth habit of *indica*, likewise an effort being made to produce the larger flowers.

During the course of the hybridization in which selections from the results of many generations of crossing nameless seedlings, were to produce the parents hereof, these were in turn crossed, the seed parent being #449 and the pollen parent #302.

My present new and distinct variety of azalea is characterized by its good budding qualities, its earliness of bloom which enables the forcing of the same for even earlier bloom, the brilliant white color of its blooms having a faint light yellow-green center with more vigorous compact growth, abundant, strong, yellow-green foliage.

Specifically availing of the Nickerson Color Fan published by The Munsell Color Company, the blooms of my new variety can only be classified as brilliant white with a faint light yellow-green center in each. As grown in the vicinity of Whitewater, Wisconsin, under uniform culture, plants of this variety are grown to an average height in a year of about 5 inches and 8 to 10 inches in two years. The average spread may be approximately 6 inches at the end of one year and 8 to 10 inches in diameter at the end of two years.

This new variety which I have developed is capable of being forced so that it is available at the Christmas season, and as such is an improvement over other whites which ordinarily are not available at that time of year.

My new variety when grown in the region of Whitewater, Wisconsin blooms early and profusely and continuously, and may be said to actually bloom very early for this particular type, having good keeping qualities and exceptionally reliable budding characteristics.

As would be expected, it is adversely affected by hot weather above 90 degrees and may develop brown spots therefor, the browning preceding wilting which may take place at the end of the third week.

My new variety has been asexually reproduced by cuttings of tips or sections of branches in the vicinity of Whitewater, Wisconsin, and said new variety has been found to retain its distinctive characteristics through successive asexual reproduction.

The accompanying drawing forming a part hereof shows a typical plant of my new variety of azalea.

The following is a detailed description of my new variety of azalea plant, the color references being to the Nickerson Color Fan published by The Munsell Color Company:

*Description*

Parentage: Seedlings #449 and #302 (unpatented, my own hybridization).

Classification: Botanic.—*Rhododendron hybrida.*

*Flower*

Blooming habit: Early, profusely and continuously. Observations were made in the vicinity of Whitewater, Wisconsin during January in the greenhouse.

Bud:
- *Size.*—Medium.
- *Form.*—Pointed.
- Bud not affected by wet weather substantially, but is affected by hot, dry weather.

Color:
- *When sepals first divide.*—White.
- *When petals begin to unfurl.*—White.
- *When half blown.*—White.
- *Sepals.*—Smooth edge—drop as bud opens.
- *Peduncle.* — Length — short. Aspect — smooth. Strength—stiff. Bud opens well but may develop brown spots at high, dry heat.

Bloom:
- *Size.*—Medium. Average size when fully expanded—2¼″.
- *Borne.*—Several together.
- *Stems.*—Short, strong.
- *Form.*—When first open — cupped. Permanence—retains its form to the end.
- *Petalage.*—Double, hose-in-hose. Number of petals under normal conditions—10 to 15.
- *Color.*—Center of flower — Light Yellow-Green 7.5GY 9/4. Outer petals—clear white. Base of petals—Light Yellow-Green 7.5GY 9/4. Inside of petals—clear white. Reverse of petals — clear white. General tonality from a distance—white.
- *Discoloration.*—Third week—browning precedes wilting, high temperatures hasten process.

Petals:
- *Texture.*—Soft; not affected by wet weather but browns in hot weather.
- *Appearance.*—Inside—satiny. Outside—satiny.
- *Form.*—Scalloped.
- *Arrangement.*—Informal.
- *Petaloids in center.*—Few.
- *Persistence.*—Hang on and dry.
- *Fragrance.*—None.
- *Lastingness.*—On the plant—long. As cut flower—fair.

Genital organs:
- *Stamens, anthers.*—None.
- *Pollen.*—None.
- *Styles.*—Columnar and medium length.
- *Ovaries.*—All enclosed in calyx.

Plant:
- *Form.*—Bush.
- *Growth.*—Vigorous, branching and compact.
- *Height.*—Approximate measurements of average—one year about 5 inches; 2 years, 8 to 10 inches.
- *Spread.*—One year—6″. Two years—8 to 10″.

Foliage:
- *Leaflets.*—Single.

*Size.*—Medium.
*Quantity.*—Abundant.
*Color.*—Upper side—Strong Yellow-Green 5GY 6/8.
Under side—Strong Yellow-Green 5GY 7/10.
*Shape.*—Oval pointed.
*Texture.*—Glossy.
*Ribs and veins.*—Light.
*Edge.*—Smooth.
Wood (new): Color—Brilliant Yellow-Green 7.5GY 8/7.
Wood (old): Color—Dark Orange-Yellow 10YR 6/8.

I claim:

A new and distinct variety of azalea plant substantially as herein disclosed, characterized as to novelty by its good budding, its earliness of bloom, facilitating forcing for earlier bloom, the brilliant white color of its blooms with faint, light yellow-green centers, and its vigorous compact growth, with abundant strong, yellow-green foliage.

No references cited.

ABRAHAM G. STONE, *Primary Examiner.*